United States Patent
Dreyfuss et al.

(10) Patent No.: US 10,299,827 B2
(45) Date of Patent: May 28, 2019

(54) ARTHROSCOPY CANNULA WITH ONE OR MORE INFLATABLE COMPONENTS

(71) Applicant: ARTHREX, INC., Naples, FL (US)

(72) Inventors: Peter Dreyfuss, Naples, FL (US); Matthew Provencher, Weston, MA (US)

(73) Assignee: ARTHREX, INC., Naples, FL (US)

( * ) Notice: Subject to any disclaimer, the term of this patent is extended or adjusted under 35 U.S.C. 154(b) by 749 days.

(21) Appl. No.: 14/708,616

(22) Filed: May 11, 2015

(65) Prior Publication Data

US 2016/0331401 A1   Nov. 17, 2016

(51) Int. Cl.
*A61B 17/34* (2006.01)
*A61B 17/00* (2006.01)

(52) U.S. Cl.
CPC ...... *A61B 17/3423* (2013.01); *A61B 17/3421* (2013.01); *A61B 2017/00557* (2013.01); *A61B 2017/3419* (2013.01); *A61B 2017/3443* (2013.01); *A61B 2017/3458* (2013.01); *A61B 2017/3486* (2013.01); *A61B 2017/3492* (2013.01)

(58) Field of Classification Search
CPC ............ A61B 17/3421; A61B 17/3439; A61B 2017/3419; A61B 2017/3492; A61B 2017/348; A61B 2017/3441; A61B 2017/3486; A61B 17/3423; A61B 2017/00557
USPC ....... 604/101.1, 103.07, 103.08, 164.02, 204
See application file for complete search history.

(56) References Cited

U.S. PATENT DOCUMENTS

| | | | |
|---|---|---|---|
| 3,253,594 A * | 5/1966 | Matthews | A61M 25/1009 604/103.03 |
| 5,163,949 A | 11/1992 | Bonutti | |
| 5,320,611 A * | 6/1994 | Bonutti | A61B 17/0401 604/264 |
| 5,632,761 A | 5/1997 | Smith et al. | |
| 5,906,577 A * | 5/1999 | Beane | A61B 42/10 600/206 |
| 6,062,223 A * | 5/2000 | Palazzo | A61M 16/04 128/207.14 |
| 6,440,120 B1 | 8/2002 | Maahs | |
| 6,443,159 B1 | 9/2002 | Fogarty et al. | |
| 6,468,292 B1 | 10/2002 | Mollenauer et al. | |
| 6,651,672 B2 * | 11/2003 | Roth | A61B 17/00234 128/898 |
| 8,038,652 B2 | 10/2011 | Morrison et al. | |
| 8,066,673 B2 | 11/2011 | Hart et al. | |
| 8,382,707 B2 * | 2/2013 | Albrecht | A61B 17/3421 604/101.01 |
| 8,388,586 B2 * | 3/2013 | Weig | A61F 2/0027 604/101.05 |
| RE44,380 E | 7/2013 | de la Torre et al. | |
| 8,679,053 B2 | 3/2014 | von Segesser | |

(Continued)

*Primary Examiner* — Eric S Gibson
*Assistant Examiner* — Marcela I Shirsat
(74) *Attorney, Agent, or Firm* — Carlson, Gaskey & Olds (57) ABSTRACT

An arthroscopy cannula according to an exemplary aspect of the present disclosure includes, among other things, a cannula body that extends along a longitudinal axis between a proximal end and a distal end and a first inflatable component attached to the cannula body and configured to move via fluid pressure between a compressed position and an expanded position.

18 Claims, 5 Drawing Sheets

(56) References Cited

U.S. PATENT DOCUMENTS

2004/0138702 A1\* 7/2004 Peartree ............ A61B 17/3421
606/213

\* cited by examiner

ARTHROSCOPY CANNULA WITH ONE OR MORE INFLATABLE COMPONENTS

BACKGROUND

This disclosure relates to an arthroscopy cannula for providing a passageway for passing surgical instruments into an arthroscopic work space. The arthroscopy cannula includes a cannula body and an inflatable component attached to the cannula body and configured to move between a compressed position and an expanded position.

Minimally invasive surgeries, such as endoscopic or arthroscopic surgeries, are performed through portals by passing a variety of surgical instruments into an internal arthroscopic work space. Arthroscopy cannulas are often inserted into such portals to provide an access point for inserting the surgical instruments into the arthroscopic work space.

SUMMARY

An arthroscopy cannula according to an exemplary aspect of the present disclosure includes, among other things, a cannula body that extends along a longitudinal axis between a proximal end and a distal end and a first inflatable component attached to the cannula body and configured to move via fluid pressure between a compressed position and an expanded position.

In a further non-limiting embodiment of the foregoing arthroscopy cannula, the cannula body includes a tube and a bowl portion.

In a further non-limiting embodiment of either of the foregoing arthroscopy cannulas, the first inflatable component is attached to the bowl portion.

In a further non-limiting embodiment of any of the foregoing arthroscopy cannulas, the tube is made of a metallic material, the bowl portion is made of a first plastic material, and the first inflatable component is made of a second plastic material.

In a further non-limiting embodiment of any of the foregoing arthroscopy cannulas, a passageway extends through the cannula body.

In a further non-limiting embodiment of any of the foregoing arthroscopy cannulas, the passageway is configured to receive a fluid, the fluid expanding the first inflatable component from the compressed position to the expanded position.

In a further non-limiting embodiment of any of the foregoing arthroscopy cannulas, at least one dam is disposed inside of the cannula body.

In a further non-limiting embodiment of any of the foregoing arthroscopy cannulas, the first inflatable component is lengthened toward the distal end in the expanded position.

In a further non-limiting embodiment of any of the foregoing arthroscopy cannulas, at least one port is formed through the cannula body.

In a further non-limiting embodiment of any of the foregoing arthroscopy cannulas, the port is formed through a bowl portion of the cannula body.

In a further non-limiting embodiment of any of the foregoing arthroscopy cannulas, a second inflatable component is attached to the cannula body.

In a further non-limiting embodiment of any of the foregoing arthroscopy cannulas, a supply tube connects between the first inflatable component and the second inflatable component.

A surgical method according to another exemplary aspect of the present disclosure includes, among other things, inserting an arthroscopy cannula through a portal formed in a body adjacent to an arthroscopic work space. The arthroscopy cannula includes a cannula body and a first inflatable component attached to the cannula body. The method further includes inflating the first inflatable component from a compressed position to an expanded position with a fluid communicated through the cannula body.

In a further non-limiting embodiment of the foregoing method, the method includes inflating a second inflatable component from a compressed position to an expanded position.

In a further non-limiting embodiment of either of the foregoing methods, the method of inflating the second inflatable component includes communicating the fluid from the first inflatable component, through a supply tube, and then into the second inflatable component.

In a further non-limiting embodiment of any of the foregoing methods, the first inflatable component is positioned adjacent an outer surface of the body in the expanded position and the second inflatable component is positioned adjacent an inner surface of the body in the expanded position.

In a further non-limiting embodiment of any of the foregoing methods, the inflating step includes communicating the fluid through a passageway of the cannula body, then through a portal formed in the cannula body, and then into the first inflatable component.

In a further non-limiting embodiment of any of the foregoing methods, the method includes inserting at least one surgical instrument through the cannula body to access the arthroscopic work space.

In a further non-limiting embodiment of any of the foregoing methods, the inserting step includes inserting the cannula body through the portal until at least a portion of a distal end of the cannula body is positioned inside the body.

In a further non-limiting embodiment of any of the foregoing methods, the inflating step includes building fluid pressure inside the first inflatable component to lengthen the first inflatable component to the expanded position.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure details an arthroscopy cannula for use during arthroscopic or endoscopic surgical procedures. The arthroscopy cannula includes a cannula body that extends along a longitudinal axis between a proximal end and a distal end. One or more inflatable components may be attached to the cannula body. The inflatable components are configured to move between a compressed position and an expanded position to prevent the cannula body from advancing further into an arthroscopic work space and/or prevent the cannula body from pulling out of the arthroscopic work space. These and other features are discussed in greater detail in the following paragraphs of this detailed description.

Figure 1:
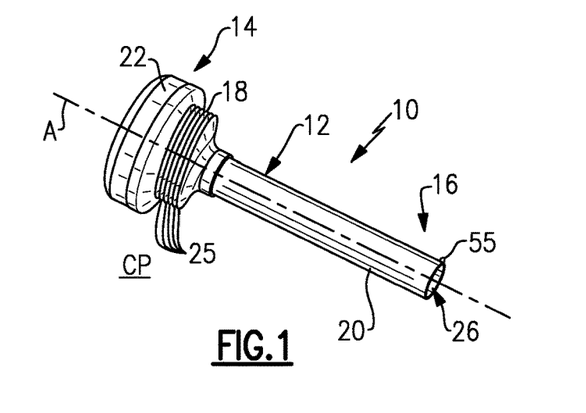
FIG. 1 illustrates an arthroscopy cannula according to a first embodiment of this disclosure.
Figure 2:
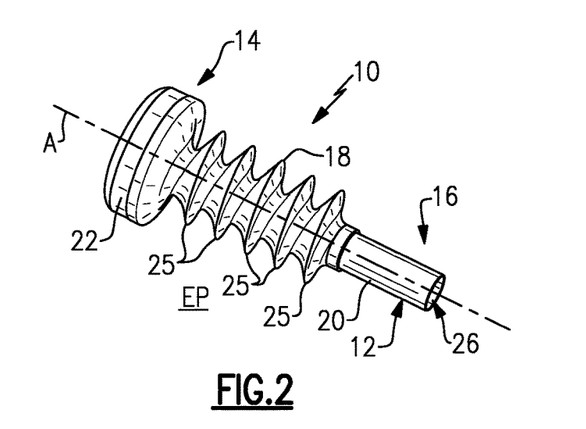
FIG. 2 illustrates another view of the arthroscopy cannula of FIG. 1.

FIGS. 1 and 2 illustrate an arthroscopy cannula 10 that may be employed during arthroscopic procedures to establish a passageway for inserting various surgical instruments into an arthroscopic work space. The arthroscopy cannula 10 includes a cannula body 12 extending along a longitudinal axis A between a proximal end 14 and a distal end 16. The proximal end 14 and the distal end 16 are portions of the cannula body 12 that are not limited to proximal-most and distal-most surfaces of the cannula body 12. An inflatable component 18, such as a balloon device, is attached to the cannula body 12.

An interference device 55 may optionally be disposed at the distal end 16 of the cannula body 12. The interference device 55 may be a nub, bump, small thread, etc. for keeping the interference device 55 from easily slipping out of an arthroscopic work space.

In a non-limiting embodiment, the cannula body 12 is a two-piece structure that includes a tube 20 and a bowl portion 22. Alternatively, the cannula body 12 could embody a single-piece structure. The tube 20 extends distally toward the distal end 16 and the bowl portion 22 extends proximally toward the proximal end 14. In a non-limiting embodiment, the bowl portion 22 has a diameter that is greater than the diameter of the tube 20. Stated another way, the bowl portion 22 includes a body that flares outwardly relative to the tube 20.

The tube 20 may be attached to the bowl portion 22. For example, the tube 20 may be received within an extension 24 (see FIGS. 4 and 5) of the bowl portion 22. Together, the bowl portion 22 and the tube 20 establish a passageway 26 for inserting one or more surgical instruments through the arthroscopy cannula 10.

In a non-limiting embodiment, the tube 20 is made of a metallic material and the bowl portion 22 is made of a plastic material. Any suitable metallic material may be used to construct the tube 20 of the cannula body 12, and any suitable plastic material may be utilized to construct the bowl portion 22 of the cannula body 12. In another embodiment, the tube 20 and the bowl portion 22 are both made of plastic materials.

Figure 9:
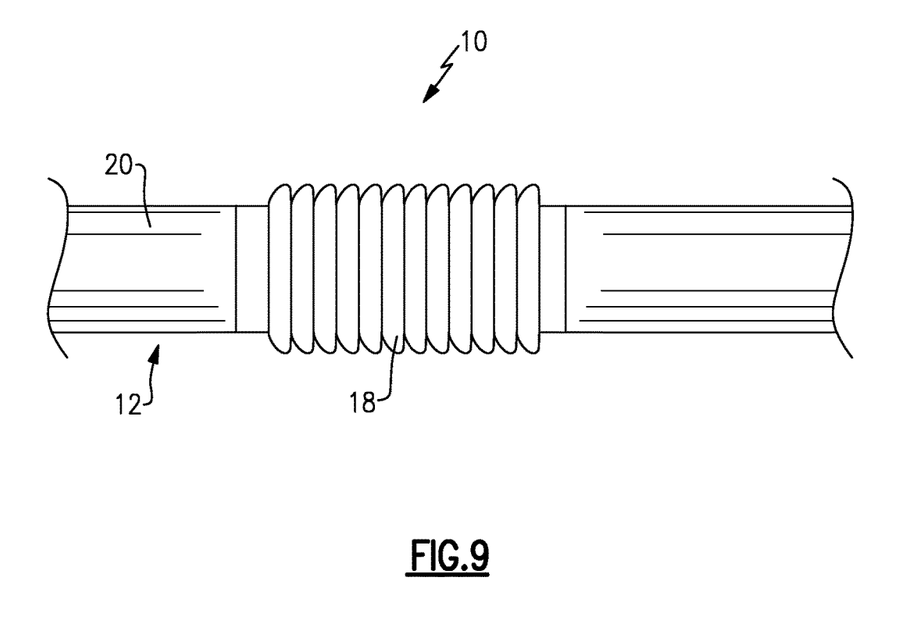
FIG. 9 illustrates an arthroscopy cannula according to yet another embodiment of this disclosure.

The inflatable component 18 may be attached to the bowl portion 22 near the proximal end 14 of the cannula body 12. In a non-limiting embodiment, the inflatable component 18 is glued to a portion of the outer surface of the bowl portion 22 of the cannula body 12. Other attachment mechanisms are also contemplated within the scope of this disclosure. In another non-limiting embodiment, the inflatable component 18 is attached to the tube 20 (see FIG. 9), or any other portion of the cannula body 12.

The inflatable component 18 may also be made of a plastic material. In a non-limiting embodiment, the plastic material used to construct the inflatable component 18 is a pliable plastic film. Non-limiting examples of suitable plastic films include polyethylene terephthalate (PET) and nylon. In another non-limiting embodiment, the plastic material of the inflatable component 18 is a different material from the plastic material of the bowl portion 22 of the cannula body 12.

In use, the inflatable component 18 of the arthroscopy cannula 10 is inflatable between a compressed position CP (shown in FIG. 1) and an expanded position EP (shown in FIG. 2). The inflatable component 18 may include a plurality of folds 25 that collapse toward one another in the compressed positon CP and expand apart from one another in the expanded position EP. In the expanded position EP, the inflatable component 18 is lengthened toward the distal end 16. The inflatable component 18 may be moved to the expanded position EP via fluid pressure that results from communicating a fluid through the arthroscopy cannula 10, as further discussed below.

Figure 3:
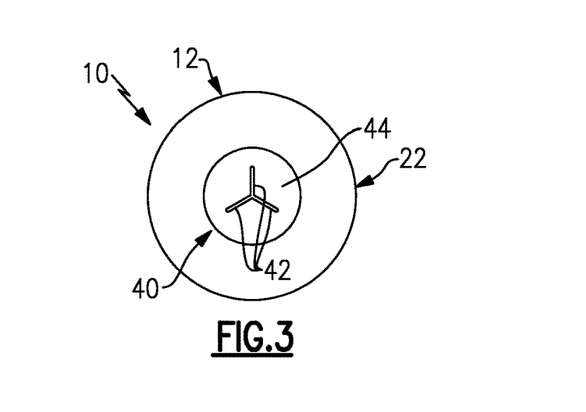
FIG. 3 is a top view of the arthroscopy cannula of FIGS. 1 and 2.

Referring now to FIG. 3, the arthroscopy cannula 10 may optionally include one or more dams 40. The dams 40 act as seals that substantially prevent fluid from spewing out of the cannula body 12. In a non-limiting embodiment, at least one dam 40 is disposed within the bowl portion 22 of the cannula body 12. Additional dams 40 could be implemented within the bowl portion 22 and/or the tube 20 of the cannula body 12. In one non-limiting embodiment, at least one dam 40 is disposed proximal to a port 28 (shown in FIGS. 4 and 5) formed in the cannula body 12. In another non-limiting embodiment, the dam 40 is formed by making slits 42 in a flexible membrane 44 of the bowl portion 22. Other dam or seal configurations are also contemplated within the scope of this disclosure.

Figure 4:
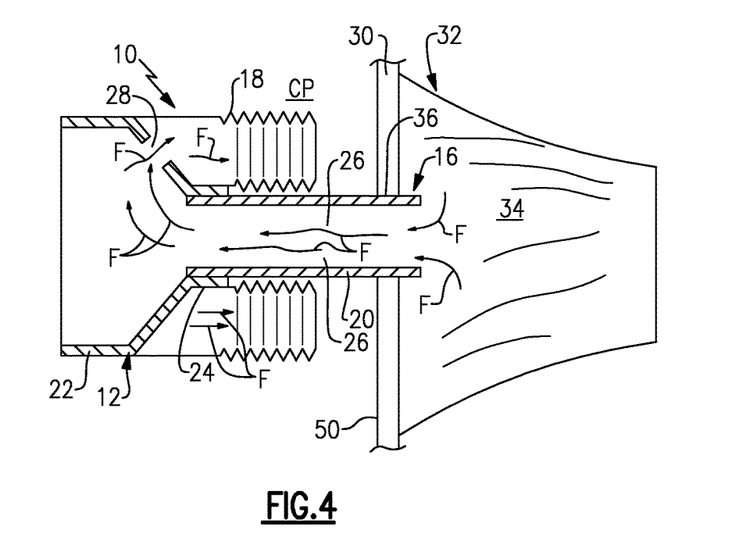
FIGS. 4 and 5 schematically illustrate the use of an arthroscopy cannula during a surgical procedure.
Figure 5:
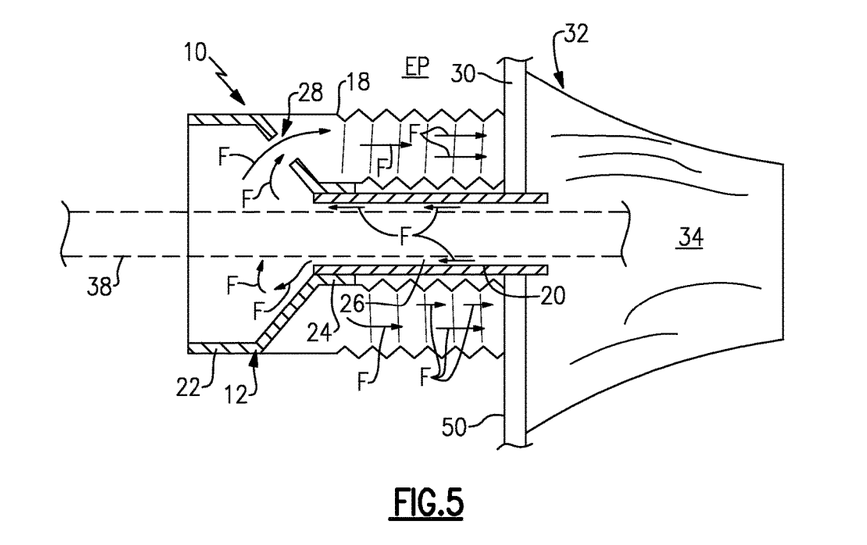

FIGS. 4 and 5, with continued reference to FIGS. 1-3, schematically illustrate a surgical method that employs the arthroscopy cannula 10. For example, the arthroscopy cannula 10 can be used during a surgical procedure to establish a passageway for inserting various surgical instruments into an arthroscopic work space 34.

Referring first to FIG. 4, the arthroscopy cannula 10 may be inserted through the skin 30 of a body 32 to access an arthroscopic work space 34 inside the body 32. For example, the tube 20 of the arthroscopy cannula 10 may be inserted through a portal 36 formed in the skin 30 until at least a portion of the distal end 16 of the cannula body 12 is positioned inside the body 32. The bowl portion 22 is entirely outside of the skin 30 and, therefore, outside of the body 32. In a non-limiting embodiment, the body 32 may be part of a knee joint, an ankle joint, a shoulder joint or any other portion of the musculoskeletal system of a human or an animal.

Fluid F from inside the body 32 may be communicated from the arthroscopic work space 34 into the passageway 26 defined by the tube 20 and the bowl portion 22 of the cannula body 12. The fluid F may be a pressurized fluid that is commonly used during arthroscopic procedures to distend and irrigate the arthroscopic work space 34. As the fluid F is communicated through the passageway 26 (in a direction that extends from the distal end 16 toward the proximal end 14), a portion of the fluid F may enter through a port 28 formed in the bowl portion 22 of the cannula body 12 to inflate the inflatable component 18 to the expanded position EP (see FIG. 5). Although only a single port 28 is shown, the cannula body 12 could include multiple ports.

Referring now primarily to FIG. 5, fluid pressure builds up inside the inflatable component 18 as the fluid F is communicated through the port 28 and into the inflatable component 18. The fluid pressure causes the inflatable component 18 to lengthen to the expanded position EP. In the expanded position EP, the inflatable component 18 may contact an outer surface 50 of the skin 30. Accordingly, when a surgical instrument 38 is inserted through the passageway 26 of the cannula body 12, the arthroscopy cannula 10 is not pushed further into the arthroscopic work space 34 because the inflatable component 18 creates interference with the outer surface 50 of the skin 30. Stated another way, the inflatable component 18 applies a constant retraction force against the outer surface 50 of the skin 30 to substantially prevent the arthroscopy cannula 10 from being pushed further into the arthroscopic work space 34. Although only a single surgical instrument 38 is shown in FIG. 5, the passageway 26 of the cannula body 12 may accommodate multiple surgical instruments.

Figure 6:
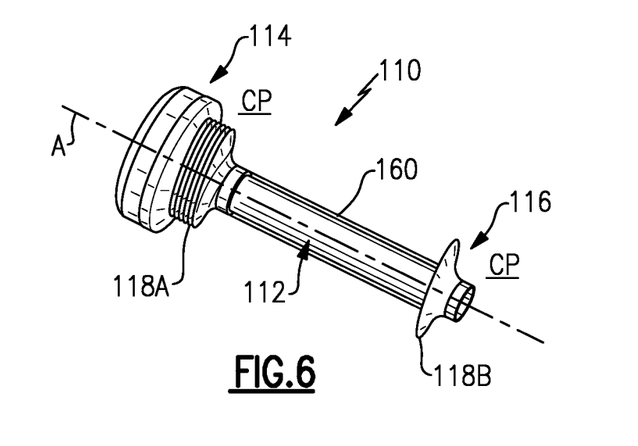
FIG. 6 illustrates an arthroscopy cannula according to another embodiment of this disclosure.
Figure 7:
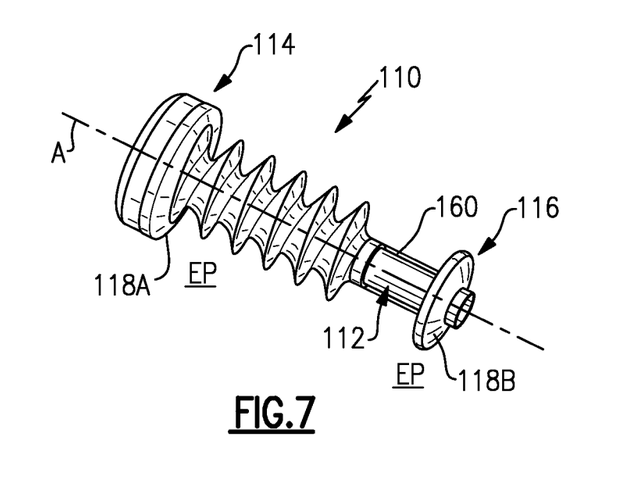
FIG. 7 illustrates another view of the arthroscopy cannula of FIG. 6.

FIGS. 6 and 7 illustrate another exemplary arthroscopy cannula 110. In this disclosure, like reference numbers designate like elements where appropriate and reference numerals with the addition of 100 or multiples thereof designate modified elements that are understood to incorporate the same features and benefits of the corresponding original elements.

The arthroscopy cannula 110 includes a cannula body 112 extending along a longitudinal axis A between a proximal end 114 and a distal end 116. A first inflatable component 118A may be attached near the proximal end 114 of the cannula body 112, and a second inflatable component 118B may be attached near the distal end 116 of the cannula body 112. In a non-limiting embodiment, the first and second inflatable components 118A, 118B are glued to the cannula body 112. A supply tube 160 may connect between the first inflatable component 118A and the second inflatable component 118B.

In use, the first and second inflatable components 118A, 118B of the arthroscopy cannula 110 are inflatable between compressed positions CP (shown in FIG. 6) and expanded positions EP (shown in FIG. 7). The first and second inflatable components 118A, 118B may be moved to the expanded positions EP via fluid pressure that results from communicating a fluid through the inside of the arthroscopy cannula 110.

Figure 8:
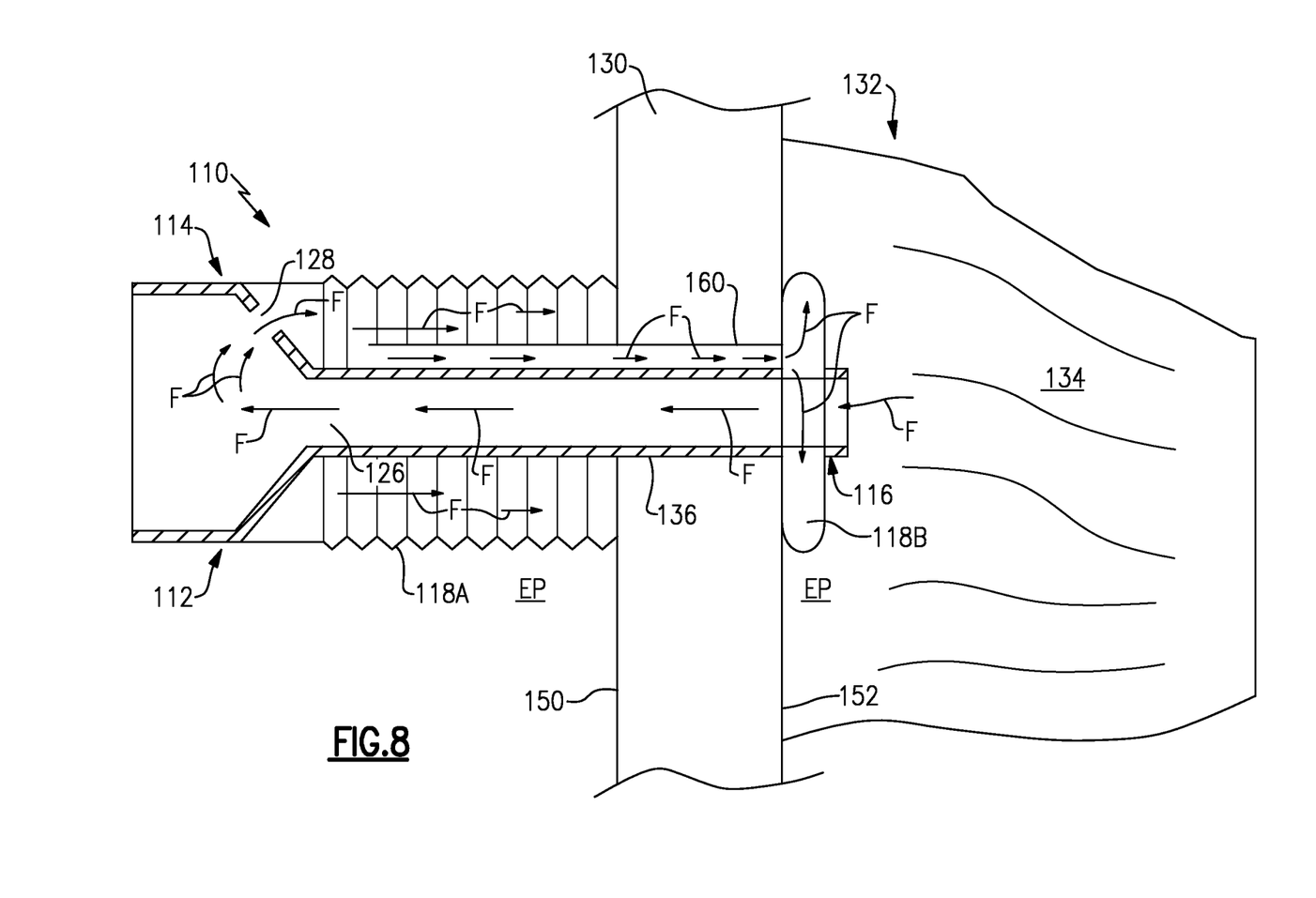
FIG. 8 illustrates inflated positions of first and second inflatable components of the arthroscopy cannula of FIGS. 6 and 7.

Referring to FIG. 8, the arthroscopy cannula 110 may be inserted through the skin 130 of a body 132 to access an arthroscopic work space 134 inside the body 132. The arthroscopy cannula 110 may be inserted through a portal 136 formed in the skin 130 until the second inflatable component 118B is positioned inside the body 132. The first inflatable component 118A is positioned outside of the body 132.

Fluid F from inside the body 132 may be communicated from the arthroscopic work space 134 into a passageway 126 defined by the cannula body 112. As the fluid F is communicated through the passageway 126 (in a direction that extends from the distal end 116 toward the proximal end 114), a portion of the fluid F may enter through a port 128 formed in proximal end 114 of the cannula body 112 to inflate the first inflatable component 118A to the expanded position EP. The fluid F may then flow through the supply tube 160 and into the second inflatable component 118B to expand it to the expanded position EP. In the expanded positions EP, the first inflatable component 118A is adjacent to and may contact an outer surface 150 of the skin 130 to keep the cannula body 112 from advancing further into the arthroscopic work space 134 and the second inflatable component 118B is adjacent to and may contact an inner surface 152 of the skin 130 to keep the cannula body 112 from pulling out of the arthroscopic work space 134.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An arthroscopy cannula, comprising:
   a cannula body that extends along a longitudinal axis between a proximal end and a distal end;
   a first inflatable component attached to said cannula body at said proximal end and configured to move via fluid pressure between a compressed position and an expanded position; and
   a port formed in the cannula body and configured to allow a fluid to pass into the first inflatable component to lengthen the first inflatable component from the compressed position to the expanded position,
   wherein said first inflatable component lengthens in a direction that is parallel to said longitudinal axis of said cannula body,
   wherein said port is arranged such that said fluid passes through an inlet located at said distal end of said cannula body prior to passing through said port.

2. The arthroscopy cannula as recited in claim 1, wherein said cannula body includes a tube and a bowl portion.

3. The arthroscopy cannula as recited in claim 2, wherein said first inflatable component is attached to said bowl portion.

4. The arthroscopy cannula as recited in claim 2, wherein said tube is made of a metallic material, said bowl portion is made of a first plastic material, and said first inflatable component is made of a second plastic material.

5. The arthroscopy cannula as recited in claim 1, comprising a passageway extending through said cannula body.

6. The arthroscopy cannula as recited in claim 5, wherein said passageway is configured to receive said fluid, said fluid expanding said first inflatable component from said compressed position to said expanded position.

7. The arthroscopy cannula as recited in claim 1, comprising at least one dam disposed inside of said cannula body.

8. The arthroscopy cannula as recited in claim 1, wherein said first inflatable component is lengthened toward said distal end in said expanded position.

9. The arthroscopy cannula as recited in claim 1, wherein said port is formed through a bowl portion of said cannula body.

10. The arthroscopy cannula as recited in claim 1, comprising a second inflatable component attached to said cannula body.

11. The arthroscopy cannula as recited in claim 10, comprising a supply tube that connects between said first inflatable component and said second inflatable component.

12. The arthroscopy cannula as recited in claim 1, wherein said port is formed through an outer wall of said cannula body.

13. An arthroscopy cannula, comprising:
   a cannula body extending along a longitudinal axis between a proximal end and a distal end;
   a bowl portion of the cannula body positioned at the proximal end;
   a tube of the cannula body extending from the bowl portion to the distal end, wherein the bowl portion flares outwardly relative to the tube;
   a first inflatable component attached directly to the bowl portion and configured to move between a compressed position and an expanded position in response to receiving a fluid, wherein the first inflatable component is closer to the distal end of the cannula body when in the expanded position and is further from the distal end when in the compressed position; and
   a port formed in the bowl portion and configured to allow said fluid to pass into said first inflatable component to lengthen said first inflatable component from said compressed position toward said expanded position,
   wherein said first inflatable component lengthens in a direction that is parallel to said longitudinal axis of said cannula body,
   wherein an inlet that is configured to receive the fluid is located at the distal end of the cannula body, and the port is located remotely from the inlet.

14. The arthroscopy cannula as recited in claim 13, comprising a nub, bump, or thread that establishes a non-inflatable interference device at the distal end of the cannula body.

15. The arthroscopy cannula as recited in claim 13, comprising a glue that attaches the first inflatable component to the bowl portion.

16. The arthroscopy cannula as recited in claim 13, wherein the first inflatable component includes a plurality of collapsible folds.

17. The arthroscopy cannula as recited in claim 13, comprising a dam disposed within the bowl portion at a location that is proximal to the port, wherein the dam is established by a flexible membrane that includes a plurality of slits.

18. The arthroscopy cannula as recited in claim 13, wherein the port extends through a flared wall of the bowl portion.

* * * * *